United States Patent [19]

Lepargneur et al.

[11] Patent Number: 5,449,612
[45] Date of Patent: Sep. 12, 1995

[54] PROCESS FOR IDENTIFYING CANDIDA BY MEANS OF CHROMOGENIC SUBSTANCES

[75] Inventors: Jean-Pierre Lepargneur, Pechabou; Geneviéve Contant épouse Pussard, Courbevoie; Jean-Luc Martinoli, Villeneuve-La-Garenne; Gérard Quentin, Colombes, all of France

[73] Assignee: Serbio, Gennevilliers, France

[21] Appl. No.: 776,257

[22] PCT Filed: Mar. 22, 1991

[86] PCT No.: PCT/FR91/00233
§ 371 Date: Nov. 19, 1991
§ 102(e) Date: Nov. 19, 1991

[87] PCT Pub. No.: WO91/14787
PCT Pub. Date: Oct. 3, 1991

[30] Foreign Application Priority Data

Mar. 23, 1990 [FR] France .................. 90 03726

[51] Int. Cl.$^6$ .................. C12Q 1/44; C12N 1/00; C07K 5/00
[52] U.S. Cl. .................. 435/18; 435/19; 435/24; 435/34; 435/254.1; 435/255.1; 435/911; 435/922; 435/944; 530/323; 530/330; 530/331

[58] Field of Search .................. 435/18, 19, 24, 34, 435/254.1, 255.1, 810, 911, 921, 922, 949, 975; 530/323, 330, 331

[56] References Cited

U.S. PATENT DOCUMENTS 4,874,695 10/1989 Pincus .................. 435/19

FOREIGN PATENT DOCUMENTS 0173944 3/1986 European Pat. Off. ....... C12Q 1/04
0255341 2/1988 European Pat. Off. .

OTHER PUBLICATIONS

Kalebuia et al., *Appl. Microbiol. Biotechnol*, vol. 28, pp. 531–536, 1988.
Iida et al., *Agric. Biol. Chem.*, vol. 52, No. 5, pp. 1281–1282, 1988.

*Primary Examiner*—Michael G. Wityshyn
*Assistant Examiner*—Abdel A. Mohamed
*Attorney, Agent, or Firm*—Jacobson, Price, Holman & Stern

[57] ABSTRACT

The present invention relates to a method of determining, assaying and identifying strains of Candida and pathogenic strains belonging to species *Torulopsis glabrata* by means of chromogenic substrates of monoamino acid or peptide type without the isolation of the strains to be identified.

21 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:1:

Gly Gly Pro Arg
1

( 2 ) INFORMATION FOR SEQ ID NO:2:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:2:

Pro Gly Pro Arg
1

( 2 ) INFORMATION FOR SEQ ID NO:3:

( i ) SEQUENCE CHARACTERISTICS:
( A ) LENGTH: 4 amino acids (B) TYPE: amino acid
(D) TOPOLOGY: linear (xi) SEQUENCE DESCRIPTION: SEQ ID NO:3:

Leu Ser Thr Arg
1

PROCESS FOR IDENTIFYING CANDIDA BY MEANS OF CHROMOGENIC SUBSTANCES

FIELD OF THE INVENTION

The present invention relates to a novel method of determining, assaying and/or identifying strains of Candida and related strains belonging to the group of the Torulopsis by means of chromogenic substrates of the monoamino acid or peptide type.

PRIOR ART

Candidiases are caused by pathogenic strains of Candida or related strains belonging mainly to the group of the Torulopsis. It is known that, in more than 60% of cases encountered, the strains of Candida responsible for candidiases belong to the species *Candida albicans* and that, in the other cases, the responsible strains belong to the other species of Candida, for example *Candida tropicalis* or *Candida krusei*, or to the group of the related strains of Torulopsis, especially the species *Torulopsis glabrata*.

It is known that, to mitigate the difficulties (large number of manipulations and long testing times) of the techniques of the prior art [blastesis test (or serum filamentation test), chlamydosporulation test on PCB or RAT media] for the identification of strains of Candida, mainly the strains of the species *Candida albicans*, and related strains, techniques have been proposed which are known in the biochemical field for detecting enzymes characteristic of yeasts, such as the osidases and aminopeptidases, and which use chromogenic or fluorogenic substrates.

Hitherto, all the techniques for identifying Candida and Torulopsis by the detection of osidases or aminopeptidases have been carried out on strains isolated beforehand.

Tests on oside substrates labeled with the fluorogenic 4-methylumbelliferyl residue (abbreviated to 4MU), i.e. especially 4MU-β-D-glucopyranoside, 4MU-2-acetamido-2-deoxy-β-D-glucopyranoside, 4MU-β-D-galactopyranoside and 4MU-2-acetamido-2-deoxy-β-D-galactopyranoside, for the purpose of detecting β-D-glucosidase, N-acetyl-β-D-glucosaminidase, β-D-galactosidase and, respectively, N-acetyl-β-D-galactosaminidase originating from strains of Candida, are known in particular from D. G. BOBEY et al., J. Clin. Microbiol., 13 (n° 2) pages 393–394 (1981), J. L. PERRY et al., J. Clin. Microbiol., 25(n° 12) pages 2424–2425 (1987), and C. M. SMITKA et al., J. Clin. Microbiol., 27 (n° 1) pages 203–206 (1989). According to these documents, the strains of Candida and Torulopsis are found not to have any β-D-galactosidase, β-L-fucosidase and β-D-glucosidase activity; the strains of *Candida albicans* and a few strains of *Candida tropicalis*, on the other hand, have an N-acetyl-β-D-galactosaminidase activity. It is clear that the use of these substrates taken in isolation is not directly applicable to the identification of strains of *Candida albicans* in a mixture of strains of Candida and, if appropriate, Torulopsis.

Also, the use of oside substrates containing a fluorogenic or chromogenic group such as p-nitrophenyl (abbreviated to PNP), β-naphthyl or 6-bromo-β-naphthyl [obtained by the coupling (with the formation of an ether bridge) of an ose with p-nitrophenol, β-naphthol or, respectively, 6-bromo-β-naphthol] for the determination of isolated strains of *Candida albicans* is known from M. CASAL et al., Mycopathologia, 81, pages 155–159 (1983), and I. POLACHEK et al., J. Clin. Microbiol., 25, pages 907–910 (1987). According to the teaching of these two documents, said oside substrates react with their target osidase originating from the strains of Candida and related strains. However, it should be pointed out that (i) the substrate β-naphthyl-N-acetyl-β-D-glucosaminide [target enzyme: N-acetyl-β-D-glucosaminidase] gives the same positive reaction with, in particular, the isolated strains of *Candida albicans*, *Candida tropicalis*, *Candida stellatoidea* and *Torulopsis glabrata*, and (ii) the substrate (6-bromo-β-naphthyl)-β-D-glucopyranoside [target enzyme: β-D-glucosidase] gives the same positive reaction with the isolated strains of *Candida albicans*, *Candida tropicalis*, *Candida pseudotropicalis*, *Torulopsis glabrata* and *Cryptococcus neoformans*. In other words, the use of these substrates cannot be directly applied to the determination of *Candida albicans* in a mixture containing other yeasts such as the Candida and Torulopsis.

As regards the use of monoamino acid or peptide substrates sensitive to the amidases and especially the aminopeptidases in the field of the identification of strains of Candida and related strains, two technical solutions are known.

The first solution, which is represented by the test marketed under the name YEAST-IDENT ™, applies to strains of yeast isolated beforehand; the method of identification is based on the determination, in a liquid medium, of the enzymic profile of the isolated strain, said profile being obtained by means of a system of about twenty different substrates after 4 h of incubation at 37° C. Said substrates, which contain a fluorogenic group such as β-naphthylamino (abbreviated to NA), are especially H-Gly-NA, H-L-Pro-NA, H-L-Trp-NA, H-L-Hyp-NA, H-L-Ile-NA, H-L-Val-NA, H-L-Leu-Gly-NA, H-L-His-NA, H-L-Cys-NA, H-L-Tyr-NA and H-Gly-Gly-NA. Interpretation is difficult with such substrates. As these substrates are specific for enzymes belonging to numerous strains of yeasts, in particular Candida, it is necessary to take into account all the results obtained with all the substrates in order to assess the enzymic profile of a given isolated strain of Candida. The use of this technical solution cannot be carried over directly to mixtures of strains; in fact, the particular substrate H-L-Pro-NA gives a positive reaction with the isolated strains of *Candida albicans*, *Candida guillermondii*, *Candida intermedia*, *Candida parapsilosis*, *Candida pseudotropicalis*, *Candida stellatoidea*, *Candida rugosa*, *Candida zeylanoides* and *Torulopsis candida*.

The second solution, described in the abstract by R. W. KELLEY et al. published in Abstr. Annu. Meet. Am. Soc. Microbiol., C 337, page 384 (1986), and in the article by J. L. PERRY et al., J. Clin. Microbiol., 28 (n° 3) pages 614–615 (March 1990), concerns the use of the afore-mentioned substrate H-L-Pro-NA in the identification of *Candida albicans* and/or *Candida tropicalis*. More precisely, said abstract C 337 indicates the possibility of distinguishing between the strains of *Candida albicans* and the strains of *Candida tropicalis* and proposes two substrates for this purpose, namely PNP-N-acetyl-β-D-galactosaminide and H-L-Pro-NA. However, this abstract neither describes the method which enables the *Candida albicans*/*Candida tropicalis* distinction to be made, nor indicates whether said method applies to mixtures of strains. The article by J. L. PERRY et al. recommends the simultaneous use of these two substrates in one and the same identification reaction in the liquid phase starting from strains isolated beforehand on a standard gelose medium.

It is known from the article by J. KUNERT et al., Journal of Medical and Veterinary Mycology, 26, pages 187-194 (1988), that chromogenic substrates which contain a monoamino acid or peptide chain and in which the chromogenic residue is the p-nitroanilino radical (abbreviated to pNA) have been studied with a view to characterizing the extracellular proteolytic enzymes of isolated strains of dermatophytes. This article mentions especially the substrate H-L-Pro-pNA but does not deal with identification of the Candida, which do not form part of the group of the dermatophytes, nor does it suggest the use of said substrate for the determination of various strains of Candida, such as those of *Candida albicans*, in a mixture of Candida and related strains.

Furthermore, it is known that patent U.S. Pat. No. 4,874,695 (publication date: 17th Oct. 1989) on the one hand indicates the possible use of the substrate H-L-Pro-pNA in the identification of strains of yeasts (see Table I, column 4, line 36), and on the other hand teaches that this substrate is not particularly specific since it is sensitive towards several strains of Candida, especially *C. albicans, C. guillermondii, C. intermedia, C. lipolytica, C. lusitanica, C. parapsilosis, C. rugosa* and *C. zeylanoides* (see Table IV, column 7, substrate n° 8). It should be pointed out that, according to said U.S. patent, (i) the strains are identified after they have been isolated (see column 2, lines 60-64), but (ii) there is no indication of how this substrate can be rendered specific for the strains of *Candida albicans*.

Consequently, the text of U.S. Pat. No. 4,874,695 in no way urges those skilled in the art to use said substrate H-L-Pro-pNA for the identification of nonisolated strains of *Candida albicans*.

SOLUTION OF THE INVENTION

According to the invention, a novel technical solution is proposed which uses chromogenic substrates for the determination of Candida and Torulopsis and which is applicable to the identification of strains, mainly the most common strains, such as *Candida albicans, Candida tropicalis, Candida krusei* and *Torulopsis glabrata* (which can be pathogenic), as well as other strains: *Candida guillermondii, Candida pseudotropicalis, Candida parapsilosis*, etc. (which are only slightly pathogenic or non-pathogenic).

More precisely, this novel solution is based, in the identification of strains of *Candida albicans* in a mixture of strains of Candida and related strains of the group of the Torulopsis, on (i) the use of a system of chromogenic substrates, and (ii) the use of a system of inhibiting means.

This technical solution offers the advantage of identifying, among the Candida and Torulopsis, (i) the strains of *Candida albicans*, which comprise mainly the pathogenic yeasts most frequently encountered in man, (ii) the strains of *Candida tropicalis* and *Torulopsis glabrata*, which are notably responsible for vaginitis, endocarditis, pneumonia and septicemia, and (iii) the strains of *Candida krusei* and *Candida guillermondii*, which can be encountered in man under certain circumstances.

AIM OF THE INVENTION

According to a first feature of the invention, a novel technical solution is proposed which uses chromogenic substrates for the determination of strains of Candida and Torulopsis, especially those most frequently encountered in man, such as *Candida albicans, Torulopsis glabrata, Candida tropicalis, Candida krusei* and *Candida guillermondii*.

According to a second feature of the invention, it is proposed, as part of this technical solution, to use a system of chromogenic substrates in order to identify, in a mixture of Candida and Torulopsis, those strains which are most frequently encountered in man and which are especially pathogenic, so as to distinguish mainly between *Candida albicans*, on the one hand, and *Torulopsis glabrata, Candida tropicalis, Candida krusei* and *Candida guillermondii*, on the other.

According to another feature of the invention, a method is proposed for the identification of the strains of Candida and Torulopsis which are most frequently encountered in man, by means of specific chromogenic substrates and a system of inhibiting means, this method being directly applicable to the determination of nonisolated strains of *Candida albicans, Torulopsis glabrata, Candida tropicalis, Candida krusei* and *Candida guillermondii*.

SUBJECT OF THE INVENTION

The aim of the invention and other advantages are achieved by the characteristics given below for the identification of the principal strains responsible for the infections of the candidiasis type which are encountered particularly in man.

A method is recommended for the identification of strains of *Candida albicans* and other related and generally pathogenic strains belonging to the group of the Candida and Torulopsis, said method, which involves the use of a chromogenic substrate and does not entail the isolation of the strains to be identified, comprising steps in which (a) a sample of strains to be identified is brought into contact with (i) at least one chromogenic substrate sensitive to at least one enzyme belonging to the group of the aminoamidases and aminopeptidases, and (ii), for the identification of *Candida albicans*, at least one inhibiting means selected from the group consisting especially of antibacterial substances, antifungal substances and mixtures thereof, in the presence of a nitrogen source, a carbon source and, if appropriate, trace elements, and (b) incubation is carried out and the kinetics of the cleavage of said substrate are observed for at least 1 h by the formation of color resulting from said cleavage.

According to another feature of the invention, a method is recommended for the identification of non-isolated strains of Candida and Torulopsis in order to distinguish between mainly the strains of *Candida albicans* and subsidiarily the strains of *Torulopsis glabrata, Candida tropicalis, Candida krusei* and *Candida guillermondii*, said method using a system of one or more chromogenic substrates and one or more inhibiting means.

Finally, according to the invention, an assay kit is recommended for the identification of said strains of *Candida albicans, Torulopsis glabrata, Candida tropicalis, Candida krusei* and *Candida guillermondii*, said kit containing at least one of said chromogenic substrates and, if necessary, one or more appropriate culture media and at least one inhibiting means.

ABBREVIATIONS

For convenience, the following abbreviations have been used in the present description:

—the amino acid residues:
Abu=2-aminobutyryl
Aib=2-aminoisobutyryl (or 2-methylalanyl)
Ala=α-alanyl
Arg=arginyl
ATC=thiazolidine-4-carbonyl (or thioprolyl)
CHA=3-cyclohexylalanyl
CHG=α-cyclohexylglycyl
CHT=3-(4-hydroxycyclohexyl)alanyl
Cys=cysteyl
Gly=glycyl
His=histidyl
Hyp=hydroxyprolyl (i.e. 3Hyp or 4Hyp)
3Hyp=3-hydroxyprolyl (or 3-hydroxypyrrolidine-2-carbonyl)
4Hyp=4-hydroxyprolyl (or 4-hydroxypyrrolidine-2-carbonyl)
Ile=isoleucyl
INC=isonipecotyl [or (piperidin-4-yl)carbonyl]
Leu=leucyl
Lys=lysyl
MeGly=N-methylglycyl (or sarcosyl)
Nle=norleucyl
Nva=norvalyl
ONC=2-oxonipecotyl [or (2-oxopiperidin-3-yl)carbonyl]
Orn=ornithinyl
Phe=phenylalanyl
Phg=phenylglycyl
Pip=pipecolinoyl
Pro=prolyl
Ser=seryl
Thr=threonyl
Trp=tryptophanyl
Val=tyrosyl
Val=valyl —the other abbreviations:
AcOH=acetic acid
Adoc=adamantyloxycarbonyl
Aoc=t-amyloxycarbonyl
Boc=t-butoxycarbonyl
(6-Br)NA=6-bromo-β-naphthylamino
Bu=n-butyl
Bz=benzoyl
Cbo=carbobenzoxy
EM=ethoxymalonyl (or EtO-CO-CH$_2$-CO)
Et=ethyl
Fmoc=fluoren-9-ylmethoxycarbonyl
Foc=furfuryloxycarbonyl
HTFA=trifluoroacetic acid
Iboc=isobornyloxycarbonyl
iPr=isopropyl
Me=methyl
MeO=methoxy
(4-MeO)NA=4-methoxy-β-naphthylamino
MM=methoxymalonyl (or MeO-CO-CH$_2$-CO)
4MU=4-methylumbelliferyl
MW=molecular weight
NA=β-naphthylamino
ONP=o-nitrophenyl
PCB=potato-carrot-bile culture medium
PEG=polyethylene glycol
Ph=phenyl
pH=cologarithm of the concentration of H$^+$ions
pNA=p-nitroanilino [or (4-NO$_2$)C$_6$H$_4$NH]
PNP=p-nitrophenyl
Pr=propyl
RAT=rice-agar-Tween culture medium
RT=room temperature (15°–20° C.)
tBu=t-butyl
Tos=p-toluenesulfonyl (or tosyl)
TTC=2,3,5-triphenyl-2H-tetrazolium chloride (or tetrazolium red)
YNB=nitrogen source marketed under the trade-name "YEAST NITROGEN BASE"
Z=benzyloxycarbonyl
Z(p-Cl)=p-chlorobenzyloxycarbonyl
Z(p-OMe)=p-methoxybenzyloxycarbonyl —the coloration and fluorescence notations:
− =none
+ =weak
++ =moderate
+++ =intense
++++ =very intense

DETAILED DESCRIPTION OF THE INVENTION

The chromogenic substrates and their addition salts useful according to the invention, which generally have a greater sensitivity than the fluorogenic substrates (presence of a substituted or unsubstituted NA group) towards the strains of Candida and Torulopsis, can be represented by the general formula $$R-(A_n)-A_1-R^a \quad (Io)$$

in which
R is the hydrogen atom or a group blocking the N-terminal end,
$A_n$ is a single bond, a monoamino acid residue or a peptide residue which can contain from 2 to 5 amino acid residues,
$A_1$ is an α-amino acid residue selected from the group consisting of the Gly, MeGly, L-Arg, L-Lys, L-His, L-Pro, L-Hyp, L-Cys, L-Val and L-Trp residues; and
$R^a$ is an aminated chromogenic residue selected especially from the group consisting of the p-nitroanilino residue and p-nitroanilino residues in which the phenyl group is substituted.

The addition salts according to the invention are essentially acid addition salts obtained by reacting a compound of formula Io with a mineral or organic acid, especially HCl, HBr, AcOH or HTFA.

The chromogenic group $R^a$ which is generally suitable for the quantitative determination of the proteolytic enzymes aminoamidases and aminopeptidases has the formula $$-NH-\underset{Y}{\underset{|}{C_6H_3}}-NO_2 \quad (II)$$

in which Y is H, Br, Cl, F, CF$_3$, COOH, COOW, CONH$_2$, CONHW, CONW$_2$, CONH(CH$_2$)$_m$NMe$_2$, HOSO$_2$, CN, OH or OW, where W is a C$_1$–C$_6$ alkyl, C$_6$–C$_{10}$ aryl, C$_7$–C$_{11}$ aralkyl or C$_3$–C$_8$ alicyclic group and m is an integer with a value of 1 to 10.

Such groups of formula II in which the phenyl ring of the pNA group is substituted are described especially in patent document EP-A-0 110 306. Among these groups, those which are useful according to the invention may be mentioned in particular: pNA, 2-carboxy-4-nitroanilino and 3-carboxy-4-nitroanilino, 2-halogeno-4-nitroanilino and 3-halogeno-4-nitroanilino (where the halogen is F, Cl or Br), 2-methoxy-5-methyl-4-nitroanilino, 2-hydroxysulfonyl-4-nitroanilino, 4-trifluoromethyl-2-nitroanilino, 4-trifluoromethyl-3nitroanilino, 4-cyano-2-nitroanilino and the like. The preferred group $R^a$ according to the invention is pNA.

The residue R is H or a group protecting the N-terminal end. Such a protecting group is well known in the art, for example one of the residues blocking the N-terminal end of peptides, such as described in patent documents EP-A-0 110 306, U.S. Pat. No. 4,480,030, FR-A-2 293 439 and U.S. Pat. No. 4,440,678. Among the groups R which are other than H, there may be indicated in particular $C_1$–$C_4$ alkyl groups (especially Me, Et, Pr, iPr, Bu, tBu), substituted or unsubstituted aryl groups (especially Ph, tolyl, xylyl, chlorophenyl, trifluoromethylphenyl, methoxyphenyl), substituted or unsubstituted aralkyl groups (especially Bzl, chlorobenzyl, dichlorobenzyl, trifluoromethylbenzyl, difluorobenzyl, methoxybenzyl, ethoxybenzyl, 3,4-methylenedioxybenzyl) and the conventional groups protecting the N-terminal end of peptides [especially Ac, Tos, Adoc, Aoc, Bz, Cbo, Fmoc, Foc, Iboc, Z, Z(p-Cl) and Z(p-OMe)].

Also suitable are residues R selected from the group consisting of (a) an oxymalonyl residue of the formula $R_1$-O-CO-$CH_2$-CO, where $R_1$ is a $C_1$–$C_4$ alkyl group, a phenyl group, a phenyl group substituted by one or more Me, MeO, Cl, Br, F or $CF_3$ groups, a $C_3$–$C_6$ cycloalkyl group, a benzyl group, a benzyl group substituted by one or more Me, MeO, Cl, Br, F or $CF_3$ groups, or a cycloalkylmethyl group in which the cycloalkyl fragment is $C_3$–$C_6$, and (b) a polyethylene glycol residue of the formula $R_2$-O($CH_2CH_2O)_n$-CO, where $R_2$ is a $C_1$–$C_6$ alkyl, phenyl or benzyl group and n is an integer with a value of 1 to 170.

In general, the preferred substrates according to the invention are those in which R is H because, with the exception of a few particular cases, especially for *Candida guillermondii* and *Torulopsis glabrata*, the presence of a group blocking the N-terminal end slows down the kinetics of cleavage by the aminoamidases or the aminopeptidases.

Among the chromogenic substrates included in formula $I_0$, there may be mentioned the substrates $$R-A_1-R^a \quad (I_1)$$

$$R-A_2-A_1-R^a \quad (I_2)$$

$$R-A_3-A_2-A_1-R^a \quad (I_3)$$

$$R-A_4-A_3-A_2-A_1-R^a \quad (I_4)$$

and their addition salts, in which R, $A_1$ and $R^a$ are defined as indicated above and $A_2$, $A_3$ *1 and A4* are each an amino acid residue.

Here, in contrast to the conventional nomenclature of peptide chains, the amino acid residues of the chromogenic substrates according to the invention are numbered 1, 2, 3 etc. from the CO-terminal end and not from the N-terminal end.

When $A_n$ is a monoamino acid residue (see formula $I_2$ for an illustration), it will advantageously be Gly, L-Pro, L-Hyp, L-ONC, L-Phg or L-ATC.

When $A_n$ is a dipeptide residue (see formula $I_3$ for an illustration), the amino acid residue in the 2 position (i.e. $A_2$) will advantageously be Gly, L-Pro, L-Hyp or L-Phg, and the amino acid residue of the N-terminal end in the 3 position (i.e. $A_3$) will advantageously be Gly, D-Pro, L-Pro, D-Hyp, L-Hyp, D-Leu, L-Leu, D-Ala, L-Ala, D-Val, L-Val, D-ONC, L-ONC or INC.

When $A_n$ is a tripeptide residue (see formula $I_4$ for an illustration), the amino acid residue in the 2 position (i.e. $A_2$) will advantageously be Gly, L-Pro, L-Hyp, L-Thr or L-Phg, the amino acid residue in the 3 position (i.e. $A_3$) will advantageously be Gly, L-Pro, L-Hyp, L-Leu, L-Ala, L-Ser or L-Val, and the amino acid residue of the N-terminal end (i.e. $A_4$) will advantageously be Gly, D-Pro, L-Pro, D-Hyp, L-Hyp, D-Leu, L-Leu, D-Ala, L-Ala, D-Val, L-Val, D-ONC, L-ONC or INC.

Advantageously, according to the invention, $A_n$ will not contain any CHA or CHT residues.

The substrates of greatest value according to the invention are generally those in which $A_n$ is a single bond or a monoamino acid, dipeptide or tripeptide residue.

Advantageously, according to the invention, $A_1$ will be L-Pro, L-Hyp, L-Arg or L-Lys, preferably L-Pro or L-Arg.

In practice, the amino acid residue of the CO-terminal end of the chromogenic substrate according to the invention will always have the L configuration; the amino acid residue in the 2 position will be a residue not containing an asymmetric carbon atom, such as Gly, or an α-amino acid residue of L configuration; the amino acid residue of the N-terminal end in a position greater than 2 will be a residue not containing an asymmetric carbon atom, such as Gly, or an α-amino acid residue of D or L configuration; any other amino acid residues present between the 2 position and the amino acid residue of the N-terminal end will either not contain an asymmetric carbon atom or will have the L configuration.

A number of chromogenic substrates capable of being used according to the invention, which were tested against several strains, have been collated in Tables I to V below. The results collated in Tables I–IV were obtained from a culture medium buffered to pH 6.0 and comprising a nitrogen source (YNB; 6.7 g/l), glucose (20 g/l), agar (20 g/l), an antibiotic (gentamycin; 0.05 g/l) and the substrate to be studied. Table I, which relates to various strains of Candida, also refers to comparative tests with fluorogenic substrates of the prior art.

These Tables show that, in general, all the substrates of formulae $I_1$, $I_2$, $I_3$ and $I_4$ in which R is H can be hydrolyzed by the aminoamidases and the aminopeptidases of the strains of *C. tropicalis*.

TABLE I

TESTS ON SUBSTRATES AGAINST STRAINS OF CANDIDA

| Substrate | Reading at 24 h | Specificity |
|---|---|---|
| H-L-Pro-pNA.AcOH | ++++ | (a) |
| H-L-4Hyp-pNA.AcOH | +++ | (a) |
| H-L-3Hyp-pNA.AcOH | +++ | (a) |
| H-L-Arg-pNA.2AcOH | +++ | (a) |
| Cbo-L-Arg-pNA.AcOH | − | |
| Z-L-Lys-pNA.AcOH | − | |
| MeO(CH₂CH₂O)₂CO-L-Arg-pNA.AcOH | − | |
| Cbo-L-Pro-pNA | − | |
| H-L-Ala-L-Pro-pNA.AcOH | ++ | (a) |
| Z-L-Ala-L-Pro-pNA | − | |
| Z-Gly-L-Pro-pNA | − | |
| H-L-Ala-L-Ala-L-Pro-pNA.AcOH | + (at | (a) |

TABLE I-continued

| | 48 h) | |
|---|---|---|
| H-Gly-L-Pro-L-Arg-pNA.2AcOH | ++++ | (b),(c) |
| Tos-Gly-L-Pro-L-Arg-pNA.AcOH | ++++ | (b),(d) |
| Boc-Gly-L-Pro-L-Arg-pNA.AcOH | ++ | (b),(d),(e) |
| H-L-4Hyp-L-Pro-L-Arg-pNA.2AcOH | ++++ | (b) |
| Boc-L-4Hyp-L-Pro-L-Arg-pNA.AcOH | ++++ | (b) |
| H-Gly-L-Pip-L-Arg-pNA.2AcOH | ++ | (b) |

TESTS ON SUBSTRATES AGAINST CANDIDA ALBICANS

| Substrate | Reading at 24 h | Specificity |
|---|---|---|
| Tos-Gly-L-Pip-L-Arg-pNA.AcOH | − | |
| H-L-Pro-L-Pro-L-Arg-pNA.2AcOH | +++ | (b) |
| H-L-ATC-L-Pro-L-Arg-pNA.2AcOH | ++ | (b) |
| H-L-Pro-NA.AcOH (f) | ++ | (a) |
| H-L-Pro-(4-MeO)NA.AcOH (f) | − | |
| H-L-Pro-(6-Br)NA.AcOH (f) | + | (a) |
| H-L-Hyp-NA.AcOH (f) | ++ | (a) |

Notes
(a): non-specific for the strains of Candida albicans
(b): interference with C. tropicalis
(c): interference with C. krusei
(d): interference with C. guillermondii
(e): interference with T. glabrata
(f): substrate of the prior art for comparison

TABLE II

TESTS ON SUBSTRATES AGAINST CANDIDA TROPICALIS

| Substrate | Reading at 24 h |
|---|---|
| H-L-Pro-L-Arg-pNA.2AcOH | ++ |
| H-L-Pro-L-Pro-L-Arg-pNA.2AcOH | ++++ |
| H-D-Pro-L-Pro-L-Arg-pNA.2AcOH | ++++ |
| H-D-Pro-D-Pro-L-Arg-pNA.2AcOH | − |
| MM-L-Pro-L-Pro-L-Arg-pNA.AcOH | + |
| H-L-Hyp-L-Arg-pNA.2AcOH | ++ |
| H-L-Hyp-L-Lys-pNA.2AcOH | ++ |
| H-L-Hyp-L-Pro-L-Arg-pNA.2AcOH | +++ |
| H-L-Hyp-L-Hyp-L-Arg-pNA.2AcOH | +++ |
| H-D-Pro-L-Hyp-L-Arg-pNA.2AcOH | +++ |
| H$_2$NCO-L-Pro-D-Pro-L-Arg-pNA.AcOH | − |
| H$_2$NCO-D-Leu-Gly-L-Arg-pNA.AcOH | ++++ |
| H-L-Leu-Gly-L-Arg-pNA.2AcOH | ++++ |
| H-L-ONC-L-Pro-L-Arg-pNA.AcOH | +++ |
| H-INC-L-Pro-L-Arg-pNA.2AcOH | +++ |
| H-Gly-L-Pro-L-Arg-pNA.2AcOH | ++++ |

TABLE III

COMPARISON OF SUBSTRATES AGAINST C. TROPICALIS AND T. GLABRATA

| Substrate | T. GLABRATA (a) | C. TROPICALIS (a) |
|---|---|---|
| EM-Gly-L-Arg-pNA.AcOH | − | ++ |
| EM-L-Phg-L-Arg-pNA.AcOH | +++ | +++ |
| EM-L-Phe-L-Arg-pNA.AcOH | − | − |
| EM-L-Tyr-L-Arg-pNA.AcOH | − | − |
| EM-L-Hyp-L-Arg-pNA.AcOH | − (b) | ++ (b) |
| EM-L-ATC-L-Arg-pNA.AcOH | − (b) | − (c) |
| H-D-Pro-L-Phg-L-Arg-pNA.2AcOH | − | ++ |
| H-Gly-L-Pro-L-Arg-pNA.2AcOH | − | ++++ |
| Boc-Gly-L-Pro-L-Arg-pNA.AcOH | +++ | + |
| Boc-L-Hyp-L-Pro-L-Arg-pNA.AcOH | − | + |
| Tos-Gly-L-Pro-L-Arg-pNA.AcOH | + | + |
| H-Gly-Gly-L-Pro-L-Arg-pNA.2AcOH (Seq. Id. No. 1) | + | + |
| H-D-Pro-Gly-L-Pro-L-Arg-pNA.2AcOH (Seq. Id. 2) | + | + |
| MM-Gly-L-Pro-L-Arg-pNA.AcOH | − | + |
| H$_2$NCO-D-Leu-Gly-L-Arg-pNA.AcOH | + | ++ |
| H$_2$NCO-L-Leu-Gly-L-Arg-pNA.AcOH | − | +++ (c) |
| BzNH-L-Ala-Gly-L-Arg-pNA.AcOH | − | +++ |
| BzNH-D-Ala-Gly-L-Arg-pNA.AcOH | − | ++ |

TABLE III-continued

COMPARISON OF SUBSTRATES AGAINST C. TROPICALIS AND T. GLABRATA

| Substrate | T. GLABRATA (a) | C. TROPICALIS (a) |
|---|---|---|
| MM-L-Phg-L-Arg-pNA.AcOH | ++++ | ++ |

Notes
(a): reading at 24 h
(b): +++ with reading at 48 h
(c): ++++ with reading at 48 h

TABLE IV

TESTS ON SUBSTRATES AGAINST CANDIDA KRUSEI

| Substrate | Reading at 24 h | Specificity |
|---|---|---|
| H-Gly-L-Pro-L-Arg-pNA.2AcOH | ++++ | (a) |
| Tos-Gly-L-Pro-L-Arg-pNA.AcOH | − | (c),(e) |
| Boc-Gly-L-Pro-L-Arg-pNA.AcOH | − | (b),(f) |
| H-L-Pro-L-Pro-L-Arg-pNA.2AcOH | − | (a) |
| H-Gly-Gly-L-Pro-L-Arg-pNA.2AcOH (Seq. Id. No. 1) | ++ | (d) |
| H-L-ONC-L-Arg-pNA.AcOH | ++ | (e) |
| MM-Gly-L-Pro-L-Arg-pNA.AcOH | +++ | (d) |

Notes
(a): interference with C. tropicalis (++++)
(b): interference with C. tropicalis (+++)
(c): interference with C. tropicalis (++)
(d): interference with C. tropicalis (+)
(e): interference with C. guillermondii (++++)
(f): interference with T. glabrata (+++)

TABLE V

TESTS ON SUBSTRATES AGAINST CANDIDA GUILLERMONDII

| Substrate | Reading at 24 h | Specificity |
|---|---|---|
| H-L-Pro-pNA.AcOH | ++++ | (a) |
| H-L-ONC-L-Arg-pNA.AcOH | ++++ | (b) |
| Tos-Gly-L-Pro-L-Arg-pNA.AcOH | ++++ | (c) |
| Boc-L-Leu-L-Ser-L-Thr-L-Arg-pNA.AcOH (Seq. Id. No. 3) | ++++ | (c) |

Notes
(a): interference with C. albicans (++++)
(b): interference with C. krusei (++)
(c): interference with C. tropicalis (++)

The chromogenic substrates collated in Tables I–V above and the Tables given below were prepared by the conventional methods of peptide synthesis, especially those described in the afore-mentioned prior art and French patent application n° 90 01965 of 19th Feb. 1990 to the Applicant.

Table I confirms that, for identification of the strains of Candida, substrates which are suitable according to the invention are selected from the group consisting of the compounds of the formula $$R-A_1-R^a \qquad (I_1)$$

in which R, $A_1$ and $R^a$ are defined as indicated above (especially H-L-Pro-pNA and H-L-Hyp-pNA) and the compounds of the formulae H-Gly-L-Pro-L-Arg-pNA,
Tos-Gly-L-Pro-L-Arg-pNA,
H-L-4Hyp-L-Pro-L-Arg-pNA,
Boc-L-4Hyp-L-Pro-L-Arg-pNA and their addition salts.

The substrates which are preferred according to the invention for identification of the strains of Candida

*albicans* will be selected from the group consisting of the compound of formula $I_1$ in which $A_1$ is L-Pro, R is H and $R^a$ is pNA, and its addition salts.

For determination of the strains of *T. glabrata*, it is recommended to use a substrate selected from the group consisting of the compounds of formula $I_2$ or $I_3$ in which $A_1$ is L-Arg, $A_2$ is L-Pro or L-Phg, $A_3$ is Gly, $R^a$ is pNA and R is other than H, and their addition salts.

Among the substrates useful for determination of the strains of *T. glabrata*, EM-L-Phg-L-Arg-pNA, MM-L-Phg-L-Arg-pNA, Boc-Gly-L-Pro-L-Arg-pNA and their addition salts are preferred according to the invention.

For identification of the strains of *C. krusei*, it is recommended to use a substrate selected from the group consisting of the compounds of formula $I_3$ in which $A_1$ is L-Arg, $A_2$ is L-Pro, $A_3$ is Gly, $R^a$ is pNA and R is H, EM or MM, and their addition salts.

The preferred substrates among those which are suitable for identification of the strains of *C. krusei* are: H-Gly-L-Pro-L-Arg-pNA, MM-Gly-L-Pro-L-Arg-pNA and their addition salts.

According to the invention, for identification of the strains of *C. guillermondii*, it will be preferable to use a substrate selected from the group consisting of the compounds of the formulae H-L-Pro-pNA,
H-L-Arg-pNA,
H-L-ONC-L-Arg-pNA,
Tos-Gly-L-Pro-L-Arg-pNA,
Boc-L-Leu-L-Ser-L-Thr-L-Arg-PNA (SEQ. ID. NO.3)

and their addition salts.

Finally, according to the invention, for determination of the strains of *C. tropicalis*, it will be advantageous to use a substrate selected from the group consisting of the compounds of formulae $I_1$, $I_2$, $I_3$ and $I_4$ in which $A_1$, $A_2$, $A_3$ and $A_4$ are defined as indicated above, $R^a$ is pNA and R is other than H, and their addition salts.

It is found that the substrates of formula $I_1$ which contain an L-Arg, L-Trp, L-Val, L-His or L-Cys residue as the amino acid $A_1$, and which are hydrolyzed by the strains of *Candida albicans*, are generally also hydrolyzed by more than 90% of the strains of *T. glabrata, C. krusei* and *C. tropicalis* (which are capable of being pathogenic). On the other hand, it has been observed, according to the invention, that the substrates of formula $I_1$ in which $A_1$ is L-Pro or L-Hyp and R is H are more specific for *C. albicans* since they are only hydrolyzed by *C. guillermondii, C. parapsilosis, C. zeylanoides* and *Tr. cutaneum* (which are only slightly pathogenic or non-pathogenic).

The specificity of the method of identification is ensured, according to the invention, by associating inhibitors with the substrate. In particular, cycloheximide, incorporated in the culture medium containing the substrate for *Candida albicans*, inhibits the growth of all the yeasts belonging to the group of the Candida and Torulopsis which interfere with the specificity of the substrate for *Candida albicans*. The few strains of *Candida zeylanoides* which are not inhibited by said cycloheximide can be selectively inhibited using maltose in preference to glucose as the carbon source in order to ensure the identification of *Candida albicans*.

To carry out the method of identification of the invention, a nutrient medium containing on the one hand a nitrogen source, a carbon source and, if appropriate, trace elements, and on the other hand at least one inhibitor selected from group consisting of antibiotic substances, is inoculated. Advantageously, the inoculation medium will be a solid medium (gelose) whereas the inoculation medium of the above-cited U.S. Pat. No. 4,874,695 is liquid.

Among the inhibitors which are suitable, there may be mentioned especially antibacterial substances (such as chloramphenicol, gentamycin and the like) and antifungal substances (such as cycloheximide and the like, which, in the presence of a specific substrate of the invention, such as H-L-Pro-pNA, only permit hydrolysis by *Candida albicans*) for eliminating the contaminants or selecting the strains which it is desired to identify. In other words, the presence of an antifungal substance, such as cycloheximide and its analogs, inhibits the growth of yeasts, including especially the Torulopsis and the other Candida, which interfere with the determination of *Candida albicans*.

The culture medium can also contain a dye, especially such as rhodamine (rhodamine 6G or rhodamine B) at a final concentration of 0.001–0.005 g/l, or an oxidation-reduction dye, especially such as a tetrazolium salt [tetrazolium red (TTC) or else tetrazolium blue] at a concentration of 0.05–0.9 g/l.

The dyes act as means of inhibiting the culture of certain Candida. In particular, rhodamine, and especially rhodamine 6G, inhibits the growth of *C. tropicalis* and the tetrazolium salt is not reduced by the strains of *T. glabrata* and *C. krusei*.

The nitrogen source will advantageously be a peptone of natural or synthetic origin. The following are particularly suitable according to the invention: the products designated under the tradenames "YEAST NITROGEN BASE" (YNB) reference 0392, NEO-PEPTONE reference 0119, PROTEOSE PEPTONE reference 0122 and BACTO PEPTONE reference 0118 (supplied by DIFCO) and the yeast extract reference 64341 (supplied by the INSTITUT PASTEUR). The peptone will be used at a concentration of 4 to 15 g/l and preferably at a concentration of 10 g/l.

The carbon source will consist of a sugar, especially glucose or maltose, at a concentration of 10 to 40 g/l. As indicated above, maltose, which permits the growth of the strains of *Candida albicans*, offers the advantage of inhibiting the growth of the strains of *Candida zeylanoides*.

The culture medium may be solid, in which case it will contain 10 to 30 g/l of agar. Examples of suitable products are those marketed under the names BACTO AGAR reference 0140, CORN MEAL AGAR reference 0386 and BITEK AGAR reference 0138 (supplied by DIFCO).

The culture medium may be buffered to pH 4.5, pH 5.0–5.5 or, preferably, pH 6.0 (0.1 M acetate buffer) or to pH 8.0 (0.1 M Tris buffer). As the strains of *Candida guillermondii* are cultivated at a pH greater than or equal to 6 and preferably in an alkaline medium, the possible interference of *C. guillermondii* with the determination of *C. albicans* can be eliminated by cultivating the isolated or non-isolated strains of *C. albicans* at a pH of 4.5–5, since the strains of *C. albicans* are generally resistant in acid media of pH 4.5–5. According to the invention, there is no need to worry about this interference when the development of yeasts other than *C. albicans* is inhibited by means of cycloheximide; in that case, it suffices to carry out the process at pH 6.0 or 8.0 in the presence of said cycloheximide.

If necessary, several substrates will be used when the mixture of non-isolated strains is capable of containing strains of C. tropicalis. Thus the C. tropicalis/T. glabrata interference can be visualized by using a first substrate for T. glabrata and a second substrate for C. tropicalis and then, if appropriate, by studying the reduction of TTC by C. tropicalis alone or by inhibiting the growth of C. tropicalis alone with rhodamine 6G.

For identification of the strains of C. guillermondii, it will be more advantageous to use a culture medium buffered to pH 8.0.

The best mode of carrying out the invention consists in (1) preparing a solid culture medium by incorporating the peptone (10 g/l), the sugar (10 to 40 g/l) and the agar (10 to 30 g/l) into 980 ml of buffer, homogenizing the resulting mixture at RT, sterilizing said mixture (especially for 0.25 h at 120°–125° C.), keeping said mixture at 45°–50° C. after sterilization for a period of less than 4 h, adding a composition of the substrate in a buffer medium, which has been sterilized beforehand by passage over a filter membrane, the concentration of the substrate being between 0.5 and 2 mM and preferably equal to 1 mM (i.e., for example, a final concentration of 0.35 g of the substrate H-L-Prop-pNA per liter of gelose), adding at least one of the following inhibitors sterilized beforehand on a membrane:

a buffered solution of gentamycin (at a final concentration of 0.03–0.06 g, preferably 0.05 g, per liter of gelose), a buffered solution of tetrazolium salt (preferably TTC at a final concentration of 0.1 g per liter of gelose), a solution of chloramphenicol (at a final concentration of 0.25 g per liter of gelose), a solution of cycloheximide (at a final concentration of 0.1–0.5 g, preferably 0.5 g, per liter of gelose) and a solution of rhodamine 6G (at a final concentration of 0.001–0.003 g per liter of gelose), dividing up the resulting mixture into a form suitable for assay (Petri dishes, tubes, strips or the like) and allowing said mixture to cool for at least 0.25 h at 20°–25° C. under a sterile atmosphere; the product thus obtained is stored at 12°–15° C. in the dark; it can be placed in appropriate bags, especially plastic bags so as to prevent any evaporation;

(2) inoculating the culture medium conditioned in this way with a colony of an isolated strain or of a mixture of strains to be studied (the inoculation can be effected either by deposition, or by streaking, or else by plating), said colony being emulsified in distilled water or isotonic solution;

(3) incubating the culture medium at a temperature of between RT and 40° C. (preferably at 37° C.) for at least 18 h, at a pH greater than or equal to 4.5 and preferably of between 6.0 and 8.0; and (4) visually observing the reaction obtained.

The incubation will generally take less than 48 h, Preferably, said incubation will be carried out at 37° C. on a solid gelose medium for 20–30 h and preferably for 24 h.

The reading of stage (3) makes it possible to assess the presence or absence of a positive reaction, a positive reaction being characterized especially by a yellow coloration, visible to the naked eye, due to the release of the preferred chromogenic residue according to the invention: H-pNA (or an orange coloration due to the presence of rhodamine), and a possible change in color of the medium to pink or violet, depending on the species of Candida, due to the reduction of the TTC.

According to the invention, the culture medium may contain one or more chromogenic substrates.

Further advantages and characteristics of the invention will be understood more clearly from the following description of practical Examples and comparative tests. These data as a whole do not in any way imply a limitation but are given by way of illustration.

EXAMPLE 1

According to the afore-mentioned best mode of carrying out the invention, a culture medium containing the following ingredients is prepared; it is called gelose 1 below and is buffered to pH 6.0.

| YNB | 6.7 g/l |
|---|---|
| Glucose | 5.0 g/l |
| Agar | 20 g/l |
| Gentamycin | 0.04 g/l |
| Chromogenic substrate | 1 mM |

EXAMPLE 2

According to the afore-mentioned best mode of carrying out the invention, a culture medium containing the following ingredients is prepared; it is called gelose 2 below and is buffered to pH 6.0.

| Modified Sabouraud's agar (SM) | 50 g/l |
|---|---|
| Gentamycin | 0.05 g/l |
| Chromogenic substrate | 1 mM |

EXAMPLE 3

According to the afore-mentioned best mode of carrying out the invention, a culture medium containing the following ingredients is prepared; it is called gelose 3 below and is buffered to pH 6.0.

| Sabouraud's dextrose agar | 65 g/l |
|---|---|
| Gentamycin | 0.05 g/l |
| TTC | 0.1 g/l |
| Cycloheximide | 0.5 g/l |
| Chromogenic substrate | 1 mM |

EXAMPLE 4

According to the afore-mentioned best mode of carrying out the invention, a culture medium containing the following ingredients is prepared; it is called gelose 4 below and is buffered to pH 6.0.

| YNB | 6.7 g/l |
|---|---|
| Glucose | 20 g/l |
| Agar | 20 g/l |
| Gentamycin | 0.05 g/l |
| Chromogenic substrate | 1 mM |

EXAMPLE 5

According to the afore-mentioned best mode of carrying out the invention, a culture medium containing the following ingredients is prepared; it is called gelose 5 below and is buffered to pH 6.0.

| | |
|---|---|
| YNB | 6.7 g/l |
| Maltose | 20 g/l |
| Agar | 20 g/l |
| Gentamycin | 0.05 g/l |
| Cycloheximide | 0.5 g/l |
| Chromogenic substrate | 1 mM |

EXAMPLE 6

Several isolated strains of *C. albicans, C. tropicalis, C. krusei, C. guillermondii, C. pseudotropicalis, C. parapsilosis, C. zeylanoides, T. glabrata* and *Trichosporon cutaneum* were inoculated and incubated on the media of Examples 1 to 5. It was found that, with the substrate H-Pro-pNA.AcOH, gelose 5 is the most appropriate for the strains of *Candida albicans*. Part of the results obtained has been collated in Table VI below, where the TTC column relates to results of tests undertaken separately on a standard gelose medium containing TTC. These results show the value of using cycloheximide to render the substrate H-L-Pro-pNA.AcOH specific for the strains of *Candida albicans*.

EXAMPLE 7

Several isolated strains of *C. albicans, C. tropicalis, C. krusei, C. guillermondii* and *T. glabrata* were inoculated and incubated on the media of Example 2 [containing either the substrate N-Ac-β-D-galactosaminide-PNP of the prior art, or the substrates H-L-PropNA.AcOH (specific for *C. albicans*), EM-L-Phg-L-ArgpNA.AcOH (specific for *T. glabrata*) and H-Gly-L-Pro-L-Arg-pNA.2AcOH (specific for *C. krusei*)]and of Example 5 (containing the substrate H-L-Pro-pNA.AcOH).

It was found that the substrates EM-L-Phg-L-Arg-pNA.AcOH and H-Gly-L-Pro-pNA.AcOH are hydrolyzed by the strains of *C. tropicalis*. The results obtained are collated in Table VII below, where the TTC column relates to results of tests undertaken separately on a standard gelose medium containing TTC.

TABLE VI

DIAGNOSIS OF *CANDIDA ALBICANS*
(from isolated colonies)
Reading at t = 24 h

| Strains | n (a) | TTC | (1) | (2) | (3) |
|---|---|---|---|---|---|
| C. albicans | 10 | pink | ++++ | ++++ | ++++ |
| C. tropicalis | 4 | mauve (d) | – | – | – |
| T. glabrata | 4 | (b) | – | – | – |
| C. krusei | 4 | (b) | – | – | – |
| C. guillermondii | 2 | (c) | – | +++ | – |
| C. zeylanoides | 1 | (c) | – | ++ | – |
| Tr. cutaneum | 1 | pink | ++ | + | – |
| C. parapsilosis | 5 | pink | – | +++ | – |
| C. pseudotropicalis | 2 | pink | – | – | – |

Notes
(a) number of strains
(b) white and slightly pink in one case
(c) white-pink
(d) of the 4 strains studied, 3 gave the result – and 1 the result +++
(1) gelose 2 containing the substrate N-Ac-β-D-galactosaminide-PNP
(2) gelose 2 containing the substrate H-L-Pro-pNA.AcOH
(3) gelose-5 containing the substrate H-L-Pro-pNA.AcOH

TABLE VII

DIAGNOSIS OF THE PRINCIPAL CANDIDA
(from isolated colonies)
Reading at t = 24 h

| Strains | n (a) | TTC | (1) | (2) | (3) | (4) | (5) |
|---|---|---|---|---|---|---|---|
| C. albicans | 6 | pink | +++ | ++++ | – | – | ++++ |
| C. tropicalis | 9 | mauve (c) | – | ++ | ++ | – |
| T. glabrata | 9 | (b) | – | – | +++ | – | – |
| C. krusei | 6 | white | – | – | – | +++ | – |

Notes
(a) number of strains
(b) white-pink
(c) reading positive (++) for only 1 of the 9 strains tested and negative for the others
(1) gelose 2 containing the substrate N-Ac-β-D-galactosaminide-PNP
(2) gelose 2 containing the substrate H-L-Pro-pNA.AcOH
(3) gelose 2 containing the substrate EM-L-Phg-L-Arg-pNA.AcOH specific for *T. glabrata*
(4) gelose 2 containing the substrate H-Gly-L-Pro-L-Arg-pNA.2AcOH specific for *C. krusei*
(5) gelose 5 containing the substrate H-L-Pro-pNA.AcOH and cycloheximide The results of Table VII show that the four principal yeasts of Candida and Torulopsis encountered in pathological cases can be identified in 24 h.

EXAMPLE 8

A mixture of several non-isolated strains of *C. albicans, C. tropicalis, C. krusei, C. guillermondii, C. pseudotropicalis, C. parapsilosis, Cryptococcus neoformaas, Torulopsis glabrata* and *Trichosporon cutaneum* was inoculated and incubated on the culture media according to Examples 1 to 5, containing the substrate N-Ac-β-D-galactosaminide-PNP of the prior art or the substrate H-Pro-pNA.AcOH according to the invention. The results, which were obtained particularly with geloses 2 and 5, are collated in Table VIII below, where the TTC column relates to results of tests undertaken separately on a standard gelose medium containing TTC.

EXAMPLE 9

A mixture of several non-isolated strains of *C. albicans, C. tropicalis, C. krusei, C. guillermondii, C. pseudotropicalis, C. parapsilosis, C. zeylanoides, C. ciferii, C. cerevisiae, Torulopsis glabrata* and *Trichosporon cutaneum* was inoculated and incubated on the culture media according to Example 5, containing the substrate N-Ac-β-D-galactosaminide-PNP of the prior art or the substrate H-Pro-pNA.AcOH according to the invention. The results, which were obtained with gelose 5, have been collated in Table IX below, which demonstrates the value of using the inhibitor—in this case cycloheximide—in association with maltose, and where the TTC column relates to results of tests undertaken separately on a standard gelose medium containing TTC.

TABLE VIII

DIAGNOSIS OF CANDIDA ALBICANS
(from non-isolated colonies)
Reading at t = 24 h
(total number of strains: 35)

| Strains | n (a) | TTC | (1) | (2) | (3) |
|---|---|---|---|---|---|
| C. albicans | 13 | (b) | ++++ | ++++ | +++ |
| T. glabrata | 8 | white | — | — | — |
| C. krusei | 6 | (c) | — | — | — |
| C. tropicalis | 1 | — | — | — | — |
| C. pseudotropicalis | 1 | pink | — | — | — |
| C. parapsilosis | 2 | pink | — | +++ | — |
| Tr. cutaneum | 2 | (d) | (e) | ++ | — |
| Cr. neoformans | 1 | — | — | — | — |
| C. guillermondii | 1 | (b) | — | +++ | — |

Notes
(a) number of strains
(b) white-mauve
(c) no culture, except for a weak culture in one case
(d) white-pink
(e) — result for 1 strain and +++ result for the other strain
(1) gelose 2 containing the substrate N-Ac-β-D-galactosaminide-PNP
(2) gelose 2 containing the substrate H-L-Pro-pNA.AcOH
(3) gelose 5 containing the substrate H-L-Pro-pNA.AcOH

TABLE IX

DIAGNOSIS OF CANDIDA ALBICANS
(from non-isolated colonies and in the presence of cycloheximide)
Reading at t = 24 h
(total number of strains: 108)

| Strains | n (a) | TTC | (1) | (2) |
|---|---|---|---|---|
| C. albicans | 89 | (b) | ++++ (c) | ++++ |
| T. glabrata | 8 | white | — | — |
| C. krusei | 1 | pink | — | — |
| C. tropicalis | 1 | mauve | — | — |
| C. pseudotropicalis | 2 | — | — | — |
| C. parapsilosis | 1 | pink | — | — |
| Tr. cutaneum | 2 | pink | — | — |
| C. zeylanoides | 1 | (d) | — | — |
| C. guillermondii | 1 | pink | — | — |
| C. ciferii | 1 | white | — | — |
| C. cerevisiae | 1 | — | — | — |

Notes
(a) number of strains
(b) pink for 87 strains, mauve for 2 strains
(c) negative for 2 out of 89 strains
(d) pink-mauve
(1) gelose 5 containing the substrate N-Ac-β-D-galactosaminide-PNP
(2) gelose 5 containing the substrate H-L-Pro-pNA.AcOH Finally, according to the invention, an assay kit is recommended which comprises at least one culture medium containing (i) the preferred substrate for the strains of Candida albicans, namely H-L-Pro-pNA or one of its acid addition salts, and (ii) cycloheximide, if appropriate substrates specific for Candida tropicalis, Candida krusei and Torulopsis glabrata, and if necessary substrates specific for the other Candida and Torulopsis.

Said culture medium will advantageously be divided up so as to present the nutrient medium (advantageously of the solid gelose type) in the form of Petri dishes, strips (nutrient medium deposited especially by coating on a paper or plastic support), tubes or plates with cups or cells.

The assay kit may also contain dilution buffers.

What is claimed is:

1. A method of identifying strains of *Candida albicans* and pathogenic strains belonging to the group of the genus Candida and species *Torulopsis glabrata*, said method, which involves the use of a chromogenic substrate and without the isolation of the strains to be identified, comprising steps in which;
   (a) a sample of strains of said Candida and *Torulopsis glabrata* to be identified is brought into contact with (i) at least one chromogenic substrate cleavable by at least one enzyme belonging to the group of the aminoamidases and aminopeptidases, and (ii) for the identification of *Candida albicans*, at least one inhibiting means selected from the group consisting of antibacterial substances, antifungal substances and mixtures thereof, in the presence of a nutrient source selected from the group consisting of a nitrogen source, a carbon source and, trace elements, and
   (b) incubation is carried out in a culture medium and the kinetics of the cleavage of said substrate are observed for at least 1 hour by the formation of color resulting from said cleavage.

2. A method according to claim 1 wherein the substrate cleavable by the aminoamidases and/or the aminopeptidases of said Candida and *Torulopsis alabrata* is selected from the group consisting of
   (i) the chromogenic substrates of the formula $$R\text{-}(A_n)\text{-}A_1\text{-}R^a \quad (I_0)$$

in which
   R is the hydrogen atom or a group blocking the N-terminal end,
   $A_n$, is a single bond, a monoamino acid residue or a peptide which can contain from 2 to 5 amino acid residues, with the condition that $A_n$ does not contain any 3-cyclohexylalanyl or 3-(4-hydroxycyclohexyl)alanyl residues,
   $A_1$ is an α-amino acid residue selected from the group consisting of Gly, MeGly, L-Arg, L-Lys, L-His, L-Pro, L-hydroxyprolyl, L-Cys, L-Val and L-Trp, and
   $R^a$ is an aminated chromogenic group selected from the group consisting of the p-nitroanilino residue and p-nitroanilino residues in which the phenyl group is substituted; and
   (ii) their addition salts.

3. A method according to claim 2 wherein, when
   (a) $A_n$ is a single bond, the chromogenic substrate is selected from the group consisting of
   (i) the compounds of the formula $$R\text{-}A_1\text{-}R^a \quad (I_1)$$

in which R and $R^a$ are defined as indicated in claim 2 and $A_1$ is L-Pro, L-hydroxyprolyl, L-Arg or L-Lys, and
   (ii) their addition salts;

(b) $A_n$ is a monoamino acid residue, the chromogenic substrate is selected from the group consisting of
   (i) the compounds of the formula $$R\text{-}A_2\text{-}A_1\text{-}R^a \quad (I_2)$$

in which R and $R^a$ are defined as indicated in claim 2, $A_1$ is L-Pro, L-hydroxyprolyl, L-Arg or L-Lys and $A_2$ is Gly, L-Pro, L-hydroxyprolyl, L-2-oxonipecotyl, L-Phe or L-thiazolidine-4-carbonyl, and
   (ii) their addition salts;

(c) $A_n$ is a dipeptide, the chromogenic substrate is selected from the group consisting of
   (i) the compounds of the formula $$R\text{-}A_3\text{-}A_2\text{-}A_1\text{-}R^a \quad (I_3)$$

in which R and $R^a$ are defined as indicated in claim 2, $A_1$ is L-Pro, L-hydroxyprolyl, L-Arg or L-Lys, $A_2$ is Gly, L-Pro, L-hydroxyprolyl, L-2-oxonipecotyl, L-phenylglycyl or L-thiazolidine-4-carbonyl and $A_2$ is Gly, D-Pro, D-hydroxyprolyl, L-hydroxyprolyl, D-Leu, L-Leu, D-Ala, L-Ala, D-Val, L-Val, [D-ONC, L-ONC or INC]D-2-oxonipecotyl, L-2-oxonipecotyl or isonipecotyl and
   (ii) their addition salts; and (d) $A_n$ is a tripeptide the chromogenic substrate is selected from the group consisting of
   (i) the compounds of the formula $$R\text{-}A_4\text{-}A_3\text{-}A_2\text{-}A_1\text{-}R^a \quad (I_4)$$

in which R and $R^a$ are defined as indicated in claim 2, $A_1$ is L-Pro, L-hydroxyprolyl, L-Arg or L-Lys, $A_2$ is Gly, L-Pro, L-hydroxyprolyl, L-2-oxonipecotyl, L-phenylglycyl, L-thiazolidine-4-carbonyl or L-Thr, $A_3$ is Gly, L-Pro, L-hydroxyprolyl, L-Leu, L-Ser, L-Ala or L-Val and $A_4$ is Gly, D-Pro, L-Pro, D-hydroxyprolyl, L-hydroxyprolyl, D-Leu, L-Leu, D-Ala, L-Ala, D-Val, L-Val, D-2-oxonipectoyl, L-2-oxonipectoyl or isonipecotyl and
   (ii) their addition salts.

4. A method according to claim 1 wherein said substrate is selected from the group consisting of
   (a) H-L-Pro- p-nitroanilino,
   (b) H-L- hydroxyprolyl-p-nitroanilino,
   (c) H-Gly-L-Pro-L-Arg- p-nitroanilino,
   (d) p-Toluenesulfonyl-Gly-L-Pro-L-Arg-p-nitroanilino,
   (e) H-L-4 hydroxyprolyl-L-Pro-L-Arg-p-nitroanilino,
   (f) Boc-L-4 hydroxyprolyl-L-Pro-L-Arg-p-nitroanilino and
   (g) their addition salts.

5. A method according to claim 1 wherein;

(a) for determination of the strains of *Candida albicans*, a substrate is used which is selected from the group of compounds of formula $$R-A_1-R^a \quad (I_1);$$

in which $R^a$ is p-nitroanilino, $A_1$ is L-Pro or L-hydroxyprolyl and R is H, and their addition salts, in the presence of cycloheximide;

(b) for determination of the strains of *Torulopsis glabrata*, a substrate is used which is selected from the group consisting of the compounds of formula $$R-A_2-A_1-R^a \ (I_2) \text{ or } R-A_3-A_2-A_1-R^{al} \ (I_3)$$

wherein in the compound of formula $I_2$ or $I_3$, $R^4$ is p-nitroanilino, $A_1$ is L-Arg, $A_2$ is L-Pro or L-phenylglycyl, $A_3$ is Gly and R is $C_1$–$C_4$ alkyl, substituted or unsubstituted aryl, substituted or unsubstituted aralkyl, or N-terminal protecting group and their addition salts;

(c) for determination of the strains of *Candida krusei*, a substrate is used which is selected from the group consisting of the compounds of formula $I_3$ in which $R^a$ is p-nitroanilino, $A_1$ is L-Arg, $A_2$ is L-Pro, $A_3$ is Gly and R is H, ethoxymalonyl or methoxymalonyl, and their addition salts;

(d) for determination of the strains of *Candida guillermondii*, a substrate is used which is selected from the group consisting of the compounds
H-L-Pro-p-nitroanilino,
H-L-Arg-p-nitroanilino,
H-L-2-oxonipecotyl-L-Arg-p-nitroanilino,
p-toluenesulfonyl-Gly-L-Pro-L-Arg-p-nitroanilino,
t-butoxy-carbonyl-L-Leu-L-Ser-L-Thr-L-Arg-p-nitroanilino (Seq. Id. No. 3) and their addition salts; and (e) for determination of the strains of *Candida tropicalis*, a substrate is used which is selected from the group consisting of the compounds of formulae $I_1$, $I_2$, $I_3$ and $$R-A_4-A_3-A_2-A_1-R^a \quad (I_4);$$

wherein in the compound of formulae $I_1$, $I_2$, $I_3$ and $I_4$, $R^a$ is p-nitroanilino, and $A_1$ is L-Pro; L-hydroxypropyl, L-Arq or L-Lys, $A_2$ is Gly, L-Pro, L-hydroxypropyl, L-2-oxonipecotyl, L-phenylglycyl, L-Thiazolidine-4-carbonyl or L-Thr, $A_3$ is Gly, L-Pro, L-hydroxyprolyl, L-Leu, L-Ser, L-Ala or L-Val and $A_4$ is Gly, D-Pro, L-Pro, D-hydroxyprolyl, L-hydroxyprolyl, D-Leu,L-Leu, D-Ala, L-Ala, D-Val, L-Val, D-2-oxonipecotyl L-2-oxonipecotyl or isonipecotyl and their addition salts; and R is $C_1$–$4$ alkyl, substituted or unsubstituted aryl, substituted or unsubstituted aralkyl, or N-terminal protecting group, and their addition salts.

6. A method according to claim 5 in which (A) the substrate for identification of the strains of *Candida albicans* is selected from the compound H-L-Pro-p-nitroanilino and its addition salts;

(B) the substrate for identification of the strains of *Torulopsis glabrata* is selected from the group consisting of the compounds ethoxymalonyl p-nitroanilino and methoxymalonyl-L-phenylglycyl-L-Arg p-nitroanilino and their addition salts;

(C) the substrate for identification of the strains of *Candida krusei* is selected from the group consisting of H-Gly-L-Pro-L-Arg-p-nitroanilino, Methoxymalonyl-Gly-L-Pro-L-Arg-p-nitroanilino and their addition salts;

(D) the substrate for identification of the strains of *Candida guillermondii* is selected from the compound of the formula
Boc-L-Leu-L-Ser-Thr-L-Arg-p-nitroanilino (Seq. Id. No. 3); and its addition salts; and (E) the substrate for identification of the strains of *Candida tropicalis* is selected from the group consisting of
H-L-Pro-L-Pro-L-Arg-p-nitroanilino,
H-D-Pro-L-Pro-L-Arg-p-nitroanilino,
H-D-Leu-Gly-L-Arg-p-nitroanilino,
H-L-Leu-Gly-L-Arg-p-nitroanilino, and their addition salts.

7. A method according to claim 5, wherein for the determination of *Torulopsis glabrata* and *Canadida albicans*, R is methyl, ethyl, propyl, isopropyl, butyl, t-butyl, phenyl, tolyl, xylyl, chlorophenyl, trifluoromethylphenyl, methoxyphenyl, benzyl, chloro-benzyl, dichlorobenzyl, trifluoromethylbenzyl, difluorobenzyl, methoxybenzyl, ethoxybenzyl, 3,4-methylenedioxybenzyl, acetyl, p-toluenesulfonyl, adamantyloxycarbonyl, t-amyloxycarbonyl, benzoyl, carbobenzoxy, fluoren-9-yl methoxycarbonyl, furfuryloxycarbonyl, isobornyloxycarbonyl, benzyloxycarbonyl, p-chlorobenzyloxycarbonyl or p-methoxybenzyloxycarbonyl.

8. A method according to claim 5, wherein for the determination of *Torulopsis glabrata* and *Candida albicans*, R is selected from a group consisting of:

a) an oxymalonyl residue of formula:

$$R_1\text{-}0\text{-}CO\text{-}CH_2\text{-}CO$$

wherein $R_1$ is $C_1$–$C_4$alkyl, phenyl, phenyl substituted by one or more methyl, methoxy, Cl, Br, F or $CF_3$,; $C_3$–$C_6$ cycloalkyl, benzyl, benzyl substituted by one or more methyl, methoxy, Cl, Br, F or $CF_3$ or a cycloalkyl-methyl in which cycloalkyl is $C_3$–$C_6$; and b) a polyethylene glycol residue of formula:

$$R_2\text{-}O(CH_2CH_2O)_n\text{-}CO$$

wherein $R_2$ is $C_{1-6}$ alkyl, phenyl or benzyl; and n is an integer 1 to 170.

9. A method according to claim 1 wherein incubation is carried out on a liquid medium at a pH of 4.5-8 and the kinetics of the cleavage of said substrate are then observed for at least 1 hour.

10. A method according to claim 9 wherein incubation is carried out at a pH equal to 4.5.

11. A method according to claim 9 wherein incubation is carried out at a pH between 6.0 to 8.0.

12. A method according to claim 1 wherein incubation is carried out on a solid gelose medium at a pH of 4.5-8 and the kinetics of the cleavage of said substrate are then observed for at least 12 hours.

13. A method according to claim 12 wherein incubation is carried out at a pH equal to 4.5.

14. A method according to claim 12 wherein incubation is carried out at a pH of between 6.0 to 8.0.

15. A method according to claim 1, wherein said culture medium is solid and contains (1) from 4 to 15 g/l of peptone;

(2) from 10 to 40 g/l of a sugar selected from the group consisting of glucose and maltose;

(3) from 10 to 30 g/l of agar; and (4) from 0.5 to 2 mmol/l of said at least one chromogenic substrate.

16. A method according to claim 15 wherein said culture medium also contains (5) from 0.1 to 0.5 g/l of cycloheximide or of inhibiting the growth of yeasts, including especially the *Torulopsis glabrata* and the Candida other than *Candida albicans*, which are capable of interfering with the identification of *Candida albicans*.

17. A method according to claim 1 and wherein the incubation is carried out at a temperature of 15° C. to 40° C.

18. A method according to any one of claim 1 and intended for the identification of non-isolated strains of *Candida albicans*.

19. A method according to claim 1 wherein the substrate cleavable by the aminoamidases and aminopeptidases of said Candida and *Torulopsis glabrata* is selected from the group consisting of (i) the chromogenic substrates of the formula $$R\text{-}(A_n)\text{-}A_1\text{-}R^a \quad (Io)$$

in which

R is the hydrogen atom or a group blocking the N-terminal end, $A_n$ is a single bond, a monoamino acid residue or a peptide which can contain 2 to 5 amino acid residues, with the condition that $A_n$ does not contain any 3-cyclohexylananyl or 3-(4-hydroxycyclohexyl)alanyl residues, $A_1$ is an α-amino acid residue selected from the group consisting of Gly, MeGly, L-Arg, L-Lys, L-His, L-Pro, L-hydroxyprolyl, L-Cys, L-Val and L-Trp, and $R^a$ is an aminated chromogenic group selected from the group consisting of the p-nitro-anilino residue and p-nitroanilino residues in which the phenyl group is substituted; and (ii) their addition salts.

20. A method according to claim 1 wherein the antibacterial substances is selected from a group consisting of chloramphenicol and gentamicin.

21. A method according to claim 1 wherein the antifungal substance is cycloheximide.

* * * * *